(12) United States Patent
Aiken

(10) Patent No.: US 7,015,210 B2
(45) Date of Patent: Mar. 21, 2006

(54) METHODS OF TREATING OPHTHALMIC DISORDERS WITH EPOXY-STEROIDAL ALDOSTERONE RECEPTOR ANTAGONISTS

(75) Inventor: James W. Aiken, Basking Ridge, NJ (US)

(73) Assignee: Pharmacia Corporation, St. Louis, MO (US)

( * ) Notice: Subject to any disclaimer, the term of this patent is extended or adjusted under 35 U.S.C. 154(b) by 4 days.

(21) Appl. No.: 10/317,650

(22) Filed: Dec. 12, 2002

(65) Prior Publication Data

US 2003/0158162 A1 Aug. 21, 2003

Related U.S. Application Data

(60) Provisional application No. 60/341,033, filed on Dec. 12, 2001.

(51) Int. Cl.
*A61K 31/56* (2006.01)
*A61K 31/58* (2006.01)
*A61K 31/585* (2006.01)

(52) U.S. Cl. ............... 514/171; 514/173; 514/172; 514/174; 514/175

(58) Field of Classification Search ......... 514/171–175
See application file for complete search history.

(56) References Cited

U.S. PATENT DOCUMENTS

| | | |
|---|---|---|
| 3,711,602 A | 1/1973 | Herschler |
| 4,177,267 A | 12/1979 | Herschler |
| 4,552,871 A | 11/1985 | Grob et al. |
| 4,559,332 A | 12/1985 | Grob et al. |
| 4,670,551 A | 6/1987 | Biollaz |
| 5,132,400 A | 7/1992 | Gammill et al. |
| 5,270,322 A | 12/1993 | Ries et al. |
| 5,385,925 A | 1/1995 | Narr et al. |
| 6,011,023 A * | 1/2000 | Clark et al. ............... 514/171 |
| 6,172,054 B1 * | 1/2001 | Clark ............... 514/179 |

FOREIGN PATENT DOCUMENTS

| | | |
|---|---|---|
| EP | 0 628 313 A1 | 12/1994 |
| WO | 95/15166 A1 | 6/1995 |
| WO | 96/40255 A2 | 12/1996 |
| WO | 01/87284 A2 | 11/2001 |
| WO | 01/95893 A1 | 12/2001 |
| WO | 02/09760 A2 | 2/2002 |

OTHER PUBLICATIONS

Antihypertensive Treatment of Heart Failure Aldosterone Antagonist, Drugs of the Future, 1999, 24(5), pp. 488-501.

* cited by examiner

*Primary Examiner*—Shengjun Wang
(74) *Attorney, Agent, or Firm*—Robert S. Thomas; Charles Ashbrook

(57) ABSTRACT

A method for treating or preventing ophthalmic disorders comprising the administration of one or more aldosterone receptor antagonists that contain a 9,11-epoxy moiety, such as eplerenone is disclosed. The method results in a reduction of intraocular pressure which treats or prevents the ophthalmic disorders. Among the disorders are intraocular hypertension, glaucoma, low tension glaucoma, age-related macular degeneration (AMD), macular edema, and diabetic retinopathy.

As glucocorticoids and mineralocorticoids also cause the retention of ions, such as sodium and potassium, where aldosterone receptors are located, aldosterone receptor antagonists that contain a 9,11-epoxy moiety, such as eplerenone, also can be administered to modulate the intraocular concentration of ions. Thus, aldosterone receptor antagonists can be administered to maintain an intraocular ionic environment that is beneficial to intraocular cell survival.

12 Claims, No Drawings

METHODS OF TREATING OPHTHALMIC DISORDERS WITH EPOXY-STEROIDAL ALDOSTERONE RECEPTOR ANTAGONISTS

CROSS-REFERENCE TO RELATED APPLICATION

This application is a complete application based on U.S. provisional application Ser. No. 60/341,033, filed Dec. 12, 2001 and the entire disclosure of which is incorporated herein by reference.

FIELD OF THE INVENTION

The present invention relates to novel methods for the treatment or prevention of glaucoma, ocular hypertension, and other ophthalmic disorders exhibiting elevated intraocular pressure, as well as ocular disorders characterized by retinal neurodegeneration or edema including glaucoma, diabetic retinopathy, and adult macular degeneration with one or more epoxy-steroidal aldosterone receptor antagonists.

BACKGROUND OF THE INVENTION

Glaucoma is a group of diseases that can lead to damage to the eye's optic nerve and result in blindness. The optic nerve connects the retina, the light-sensitive layer of nerve cells at the back of the eye, with the brain. A healthy optic nerve is necessary for good vision.

A common characteristic of glaucoma is increased intraocular pressure, excavation of the optic nerve head and gradual loss of the visual field. An abnormally high intraocular pressure ("IOP") is commonly known to be detrimental to the eye, and there are clear indications that, in glaucoma patients, this probably is the most important factor causing degenerative changes in the retina. Unless treated successfully, glaucoma will eventually lead to blindness. Its course towards that stage is typically slow with progressive loss of the vision.

In the eye, a clear fluid called aqueous humor continuously flows into and out of a space near the front of the eye called the anterior chamber to nourish nearby tissue. The fluid leaves the anterior chamber through a meshwork of tissue at the angle where the cornea meets the iris. When everything functions correctly, the angle is open, pressure is normal, and inflow equals outflow.

Open-angle glaucoma is a form of glaucoma that gets its name because the angle where the cornea meets the iris is "open," but the fluid passes too slowly out through the meshwork of tissue. Consequently, pressure rises until outflow again equals inflow, but now at a pressure that is elevated above normal. In many people, increased pressure inside the eye causes glaucoma (optic nerve damage). With early treatment to lower pressure one can often protect eyes against serious vision loss and blindness. Open-angle glaucoma is the most common form of glaucoma.

If the angle is closed and fluid cannot escape, however, continuous inflow causes the pressure to rise in the chamber. When this happens, a medical emergency is present that must be treated by surgery to open an exit passage for the aqueous humor.

Spironolactone, a nonspecific aldosterone receptor antagonist, was reported to lower IOP in glaucoma patients (Klin Monatsbl Augenheilkd, 176(3):445–6, (March 1980)). One other group has written about the possible role of aldosterone in glaucoma (Sevcik J., Pullmann R., Pitiova G., Cesk Oftalmol, 37(2):111–5, (March, 1981)).

Spironolactone, however, has antiandrogenic activity that can result in gynecomastia and impotence in men and weak progestational activity that can produce menstrual irregularities in women.

Accordingly, there is interest in development of additional active aldosterone receptor antagonists that do not interact with other steroid receptor systems such as glucocorticoid, progestin and androgen steroid receptor systems and/or that provide for a broader range of treatment. Preferably, such antagonists would be selective for aldosterone receptors.

SUMMARY OF THE INVENTION

In accordance with the present invention, therefore, a method of treating or preventing elevated intraocular pressure is provided comprising administering epoxy-steroidal aldosterone receptor antagonists. In one embodiment, the epoxy-steroidal aldosterone receptor antagonists contain a 9,11-epoxy moiety.

Also provided is a method to treat intraocular hypertension, glaucoma, low tension glaucoma, age-related macular degeneration (AMD), macular edema, and diabetic retinopathy comprising administering epoxy-steroidal aldosterone receptor antagonists. In one embodiment, the aldosterone receptor antagonists are epoxy-steroidal aldosterone receptor antagonists that contain a 9,11-epoxy moiety.

The present invention is further directed to a method to modulate the intraocular sodium and potassium ion concentrations through administering epoxy-steroidal aldosterone receptor antagonists. In one embodiment, epoxy-steroidal aldosterone receptor antagonists that contain a 9,11-epoxy moiety are administered. In another embodiment, eplerenone is administered.

The present invention is also directed to a method of treating or preventing an ophthalmic disorder comprising coadministering an epoxy-steroidal aldosterone receptor antagonist and latanoprost.

The present invention is further directed to a composition for treating or preventing an ophthalmic disorder comprising an epoxy-steroidal aldosterone receptor antagonist and latanoprost.

The present invention is still further directed to a kit for treating or preventing an ophthalmic disorder comprising an epoxy-steroidal aldosterone receptor antagonist and a second compound that affects intraocular pressure.

Other aspects and features of this invention will be in part apparent and in part pointed out hereinafter.

DETAILED DESCRIPTION OF THE PREFERRED EMBODIMENTS

The present invention relates to the treatment of elevated IOP through the use of epoxy-steroidal aldosterone receptor antagonists. In one embodiment, the epoxy-steroidal aldosterone receptor antagonist is an epoxy-steroidal aldosterone receptor antagonist containing a 9,11-epoxy moiety. In another embodiment, the epoxy-steroidal aldosterone receptor antagonist containing a 9,11-epoxy moiety is pregn-4-ene-7,21-dicarboxylic acid, 9,11-epoxy-17-hydroxy-3-oxo-, γ-lactone, methyl ester, $(7\alpha,11\alpha,17\alpha)$-, also known as eplerenone or epoxymexrenone.

The treatment includes the administration of one or more epoxy-steroidal aldosterone receptor antagonists, 20-spirox ane compounds characterized by the presence of a 9,11-substituted epoxy moiety, and/or eplerenone, that bind to aldosterone receptors or mineralocorticoid receptors (hereinafter collectively referred to as "aldosterone receptors") present in the eye. The present invention also relates to the use of epoxy-steroidal aldosterone receptor antagonists, 20-spiroxane compounds characterized by the presence of a 9,11-substituted epoxy moiety, or eplerenone, in the treatment of intraocular imbalance of ions which, if left untreated, can result in cell death in the eye.

Epoxy-Steroidal Compounds

The epoxy-steroidal aldosterone receptor antagonist compounds used in the methods of the present invention generally have a steroidal nucleus substituted with an epoxy-type moiety. The term "epoxy-type" moiety is intended to embrace any moiety characterized by having an oxygen atom as a bridge between two carbon atoms, examples of which include the following moieties:

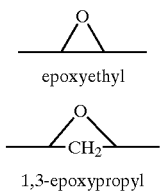

epoxyethyl 1,3-epoxypropyl

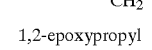

1,2-epoxypropyl

The term "steroidal", as used in the phrase "epoxy-steroidal", denotes a nucleus provided by a cyclopentenophenanthrene moiety, having the conventional "A", "B", "C," and "D" rings. The epoxy-type moiety may be attached to the cyclopentenophenanthrene nucleus at any attachable or substitutable positions, that is, fused to one of the rings of the steroidal nucleus or the moiety may be substituted on a ring member of the ring system. The phrase "epoxy-steroidal" is intended to embrace a steroidal nucleus having one or a plurality of epoxy-type moieties attached thereto.

In one embodiment of the present method, epoxy-steroidal aldosterone receptor antagonists having an epoxy moiety fused to the "C" ring of the steroidal nucleus are used. In another embodiment, 20-spiroxane compounds characterized by the presence of a 9,11-substituted epoxy moiety are used in the present methods of treatment. Compounds 1 through 11 listed in Table 1 below are illustrative 9,11-epoxy-steroidal compounds that may be used in the present methods. These epoxy steroids may be prepared by procedures described in Grob et al., U.S. Pat. No. 4,559,332, which is herein incorporated by reference in its entirety. Additional processes for the preparation of 9,11-epoxy-steroidal compounds and their salts are disclosed in Ng et al., WO97/21720 and Ng et al., WO98/25948.

TABLE 1

9,11-Epoxy-Steroidal Aldosterone receptor antagonist Compounds

| Compound # | Structure | Name |
|---|---|---|
| 1 | 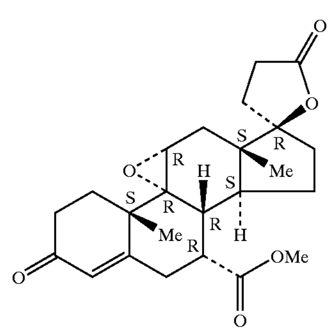 | Pregn-4-ene-7,21-dicarboxylic acid, 9,11-epoxy-17-hydroxy-3-oxo-, γ-lactone, methyl ester, (7α,11α,17β)- |
| 2 | 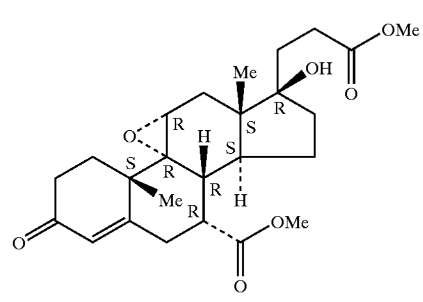 | Pregn-4-ene-7,21-dicarboxylic acid, 9,11-epoxy-17-hydroxy-3-oxo-, dimethyl ester, (7α,11α,17β)- |

TABLE 1-continued 9,11-Epoxy-Steroidal Aldosterone receptor antagonist Compounds

| Compound # | Structure | Name |
|---|---|---|
| 3 | 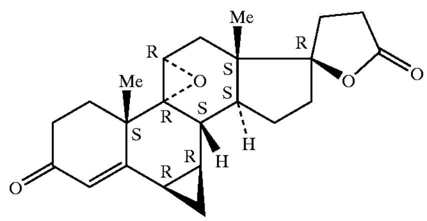 | 3'H-cyclopropa[6,7]pregna-4,6-diene-21-carboxylic acid, 9,11-epoxy-6,7-dihydro-17-hydroxy-3-oxo-, γ-lactone, (6β,7β,11α,17β)- |
| 4 | 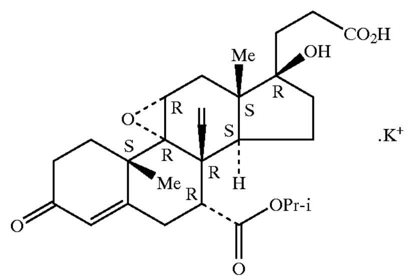 | Pregn-4-ene-7,21-dicarboxylic acid, 9,11-epoxy-17-hydroxy-3-oxo-, 7-(1-methylethyl) ester, monopotassium salt, (7α,11α,17β)- |
| 5 | 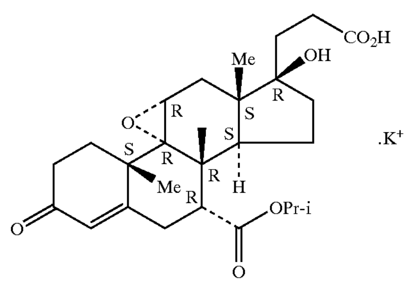 | Pregn-4-ene-7,21-dicarboxylic acid, 9,11-epoxy-17-hydroxy-3-oxo-, 7-methylethyl) ester, monopotassium salt, (7α,11α,17β)- |
| 6 | 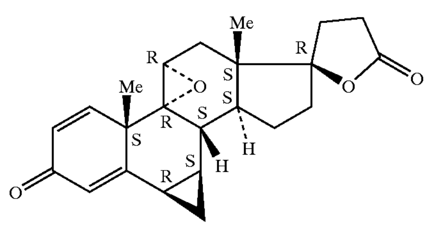 | 3'H-cyclopropa[6,7]pregna-1,4,6-triene-21-carboxylicacid, 9,11-epoxy-6,7-dihydro-17-hydroxy-3-oxo-, γ-lactone(6β,7β,11α)- |
| 7 | 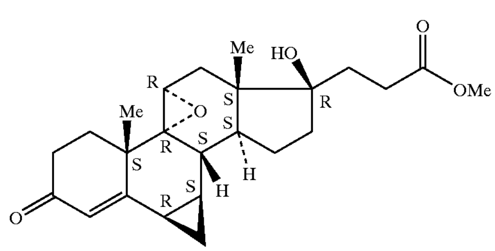 | 3'H-cyclopropa[6,7]pregna-4,6-diene-21-carboxylic acid, 9,11-epoxy-6,7-dihydro-17-hydroxy-3-oxo-, methyl ester, (6β,7β,11α,17β)- |
| 8 | 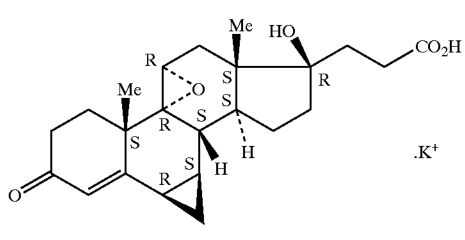 | 3'H-cyclopropa[6,7]pregna-4,6-diene-21-carboxylic acid, 9,11-epoxy-6,7-dihydro-17-hydroxy-3-oxo-, monopotassium salt, (6β,7β,11α,17β)- |

TABLE 1-continued

9,11-Epoxy-Steroidal Aldosterone receptor antagonist Compounds

| Compound # | Structure | Name |
|---|---|---|
| 9 | 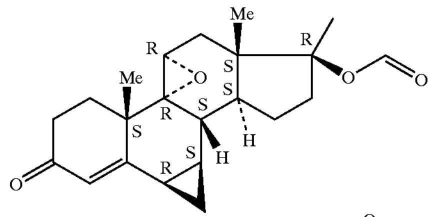 | 3'H-cyclopropa[6,7]pregna-1,4,6-triene-21-carboxylic acid, 9,11-epoxy-6,7-dihydro-17-hydroxy-3-oxo-, γ-lactone (6β,7β,11α,17β)- |
| 10 | 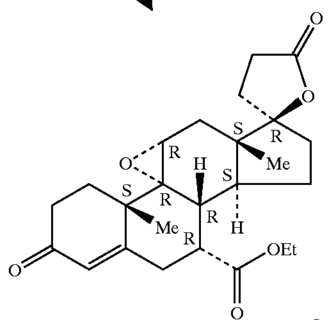 | Pregn-4-ene-7,21-dicarboxylic acid, 9,11-epoxy-17-hydroxy-3-oxo-, γ-lactone, ethyl ester, (7α,11α,17β)- |
| 11 | 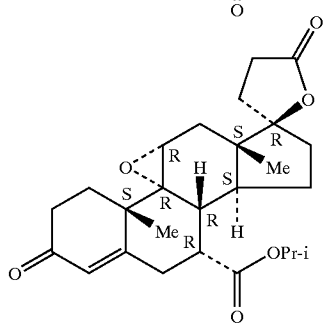 | Pregn-4-ene-7,21-dicarboxylic acid, 9,11-epoxy-17-hydroxy-3-oxo-, γ-lactone, 1-methylethyl ester (7α,11α,17β)- |

The 9,11-epoxy-steroidal aldosterone receptor antagonist compound pregn-4-ene-7,21-dicarboxylic acid, 9,11-epoxy-17-hydroxy-3-oxo-, γ-lactone, methyl ester, (7α,11α,17α)-, having the structure (I), and commonly known as eplerenone (CAS No. 107724-20-9), was first reported in U.S. Pat. No. 4,559,332 to Grob et al., which discloses a class of 9,11-epoxy-steroid compounds and their salts. Eplerenone is an aldosterone receptor antagonist and can be administered in a therapeutically effective amount where use of an aldosterone receptor antagonist is indicated, such as in treatment of pathological conditions associated with hyperaldosteronism including hypertension, heart failure including cardiac insufficiency, and cirrhosis of the liver.

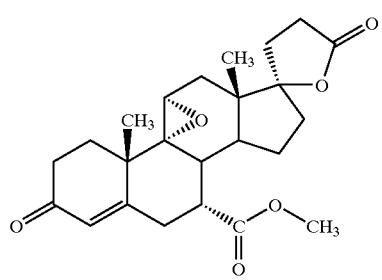

(I)

U.S. Pat. No. 4,559,332, generally discloses preparation of eplerenone and preparation of pharmaceutical compositions comprising eplerenone.

Additional processes for the preparation of 9,11-epoxy steroid compounds and their salts, including eplerenone, are disclosed in International Patent Publications No. WO 97/21720 and No. WO 98/25948.

Lowering IOP with Epoxy-Steroidal Aldosterone Receptor Antagonists

The roles of aldosterone and glucocorticoid receptors, and the roles of two enzymes, type-1 and type-2 11-beta hydroxysteroid dehydrogenase, in regulating the amount of locally active cortisol, also known as hydrocortisone, and cortisone at glucocorticoid receptors, have been known for body tissues. Hydrocortisone can bind with equal or better affinity as mineralocorticoids to the aldosterone receptor. As such, a mechanism has evolved to protect the receptor from high levels of endogenous corticosteroids. The type-2 HSD enzyme inactivates hydrocortisone to the relatively inactive corticosterone thereby permitting mineralocorticoids, such as aldosterone, to bind to the aldosterone receptors and elicit a hormonal effect.

Only recently, however, has information about the localization of these relevant molecules been available for the eye tissues. Both type-2 11-beta-HSD and aldosterone receptor immunoreactivity have been detected in non-pigmented epithelium of the ciliary body of the eye. This places the biological system in the correct location to modulate aqueous humor production. Hence, the aldosterone receptor is being protected from high hydrocortisone by the presence of the type-2 HSD. Any defect in the enzyme, however, would expose the aldosterone receptor to endogenous hydrocortisone and inappropriately stimulate aqueous humor production. The administration of an epoxy-steroidal aldosterone receptor antagonist, such as aldosterone receptor antagonists that contain a 9,11-epoxy moiety, such as eplerenone, would thereby block this undesirable effect.

IOP can be lowered by either decreasing inflow of aqueous humor or increasing outflow in the eye. Mineralocorticoid antagonists that bind to the aldosterone receptors in the eye prevent binding of both hydrocortisone and aldosterone to the receptors. The hormone receptors for aldosterone, referred to as aldosterone receptors, are present on the tissues responsible for formation of aqueous humor (Stokes et al., 2000: Schwartz & Wysocki, 1997)). Stimulation of these receptors by natural hormones, either aldosterone itself or corticosteroids having affinity for the aldosterone receptors, increases aqueous humor formation causing inflow. Therefore, the binding of the aldosterone receptors with epoxy-steroidal aldosterone receptor antagonists is a potential method for reducing aqueous inflow and thus treating diseases where elevated IOP is an indication, such as glaucoma. In another embodiment, epoxy-steroidal aldosterone receptor antagonists that contain a 9,11-epoxy moiety are administered to bind the aldosterone receptors. In another embodiment, 9,11-epoxy-steroidal aldosterone receptor antagonists described in Table 1 are administered to bind the aldosterone receptors. In still another embodiment, eplerenone is administered to bind the aldosterone receptors.

The intraocular pressure (IOP) lowering effects and potential side-effects of epoxy-steroidal aldosterone receptor antagonists can be tested in cats, monkeys and rabbits using methods described in Resul B, Stjernschantz et al. Structure-activity relationships and receptor profilins of some ocular hypotensive prostanoids. Surv of ophthalmol 1997, 41 (suppl 2) S47–S52 and Serle J B, Podos S M et al. A comparative study of latanoprost, sold under the trademark XALATAN, (Pharmacia, Skokie, Ill.), and isopropyl unoprostone (Rescular) in normal and glaucomatous monkey eyes. Jpn J ophthalmol 1998; 42:95–100. The active ingredient (or a pro-drug) can be tested in these model systems using either eye drops or systemic (oral, intravenous, percutaneous) administration.

Combination Therapy

Compositions and methods of the invention can be used in co-therapy with one or more drugs other than epoxy-steroidal aldosterone receptor antagonists. Such drugs other than epoxy-steroidal aldosterone receptor antagonists can be co-administered together with a composition of the invention. A composition of the invention can itself further comprise, in co-formulation with a first drug that is a epoxy-steroidal aldosterone receptor antagonist as described herein, a therapeutically or prophylactically effective amount of a second drug that is other than a epoxy-steroidal aldosterone receptor antagonist. This second drug can cooperate with the first drug in treating or preventing an elevated IOP condition, or it can be used to treat a related or unrelated condition simultaneously affecting the eye.

Without being held to a specific mechanism of action for the present combination therapy, it is hypothesized that the administration of epoxy-steroidal aldosterone receptor antagonists in combination with one or more other compounds or drugs that also reduce IOP is effective because of the simultaneous and interrelated responses in the eye to these two distinct classes of drugs: reduced IOP due to the reduction in aqueous humor production in response to the epoxy-steroidal aldosterone receptor antagonist and reduced IOP due to the properties and different mechanisms of actions for the one or more other co-administered compounds or drugs. As a result of the combination treatment, epoxy-steroidal aldosterone receptor antagonists such as eplerenone should produce complementary therapeutic effects because its mechanism of action is different from and complementary to these drugs. The combination of eplerenone with one or more other compounds or drugs may permit the reduction of the dosage of eplerenone and/or one or more of the administered compounds thereby reducing potential side effects.

Epoxy-steroidal aldosterone receptor antagonists can be tested in combination with one or more anti-glaucoma agents or other compounds or drugs used to lower IOP. Without being held to any particular mechanism, anti-glaucoma agents or other compounds or drugs may lower IOP by accelerating the outflow of aqueous humor from the anterior chamber or by reducing inflow of aqueous humor into the anterior chamber. As previously described, epoxy-steroidal aldosterone receptor antagonists act by inhibiting the production of aqueous humor and thereby reduce inflow of aqueous humor into the anterior chamber.

Thus, it is hypothesized that the combination therapy of epoxy-steroidal aldosterone receptor antagonists and anti-glaucoma agents or other compounds or drugs that accelerate the outflow of aqueous humor from the anterior chamber will lower IOP in an additive or synergetic manner. It is further hypothesized that a combination therapy of epoxy-steroidal aldosterone receptor antagonists and anti-glaucoma agents or other compounds or drugs that also reduce inflow of aqueous humor into the anterior chamber will lower IOP in an additive manner. In addition to the benefits of additive or synergetic effects, combination therapy, as discussed further above, may permit a lower dosage of each compound to be administered, thereby creating the possibility of reducing undesired side effects of administering a higher dosage of a single compound.

Anti-glaucoma agents or other compounds or drugs that accelerate the outflow of aqueous humor from the anterior chamber include cytoskeletal disrupting agents and prostaglandin compounds. Examples of prostaglandin compounds and their analogues include PGA, PGB, PGD, PGE, PGF, their derivatives, examples of which are disclosed in U.S. Pat. No. 5,422,368 which is herein incorporated by reference in its entirety, latanoprost (Xalatan), a combination of latanoprost, a prostaglandins, (0.005% solution) and timilol, a sympathomimetic, (0.25% solution) sold under the trademark XALCOM, (Pharmacia, Skokie, Ill.); unoprostone isopropyl ophthalmic solution, sold under the trademark Rescula, (Novartis Ophthalmics, Duluth, Ga.); lumigan, travaprost, unoprostone, $PGF2_\alpha$ agonists, prostanoids, prostaglandin pro-drugs and combinations thereof.

Anti-glaucoma agents or other compounds or drugs that inhibit or reduce inflow of aqueous humor include cholinergic agents, sympathomimetics, carbonic anhydrase inhibitors and others. Examples of these agents, compounds or drugs include cholinergic agents such as carbacol, sold under the trademark Isopto Carbachol, (Alcon, Fort Worth, Tex.), pilocarpine hydrochloride, sold under the trademark Isopto Carpine, (Alcon, Fort Worth, Tex.), muscarinic (acetylcholine) agonists such as pilocarpine, other M1 and M3 selective agonists, and combinations thereof; sympathomimetics such as beta-adrenergic antagonists such as timolol, (sold under the trademark Timooptic and Timoptic-XE), betagan, betaxolol, selective and unselective combined alpha- and beta-adrenergic antagonists, selective beta 2 adrenergic inhibitors, timolol ophthalmic solution, sold under the trademark Betinol, (Santen Incorporated, Napa, Calif.), dichlorphenamide, sold under the trademark Daranide, (Merck & Co., Inc., West Point, Pa.), apraclonidine, sold under the trademark Iopidine, (Alcon, Fort Worth, Tex.), selective and unselective alpha-adrenergic antagonists, such as brimonidine (sold under the trademark Alphagan and Alphagan P), betaxolol hydrochloride, sold under the trademark Betoptic and Betoptic S, (Alcon, Fort Worth, Tex.), carteolol hydrochloride, sold under the trademark Ocupress, (Otsuka America Pharmaceutical, Inc., Rockville, Md.), clonidine, apraclonidine, epinephrine, and combinations thereof; carbonic anhydrase inhibitors such as acetazolamide, sold under the trademark Diamox and Diamox Sequels, (Lederle Parenterals, Inc.), methazolamide, sold under the trademark Neptazane, (Lederle Parenterals, Inc., Philadelphia, Pa.), dorzolamide hydrochloride ophthalmic solution, sold under the trademark Trusopt, (Merck & Co., Inc., West Point, Pa.), dorzolamide hydrochloride-timolol maleate ophthalmic solution, sold under the trademark Cosopt, (Merck & Co., Inc., West Point, Pa.), brinzolamide hydrochloride, sold under the trademark Azopt, (Alcon, Fort Worth, Tex.), dorzolamide, brinzolamide, all carbonic anhydrase I, II, and IV isozyme inhibitors, and combinations thereof.

Other anti-glaucoma agents or other compounds or drugs that may be used to reduce IOP include cannabinoids drug class, for example, anandamine; selective and unselective PKC inhibitors drug class; rho kinase inhibitors drug class; and combinations thereof; corticosteroid receptor antagonists; selective and nonselective dopamine DA-1 agonists; TNF antagonists; somatostatin selective sst4 agonists; angiotensin II antagonists; thyroxine; adenosine 3 antagonists, vacuolar proton ATPase inhibitors such as bafilomycin; sodium hydrogen antiporter inhibitors; chloride anion exchanger inhibitors; and combinations thereof.

Administration

In one embodiment, the present invention comprises a method for the treatment or prevention of elevated IOP comprising administering to a subject a first amount of an epoxy-steroidal aldosterone receptor antagonist, an epoxy-steroidal aldosterone receptor antagonist containing a 9,11-epoxy moiety, a 9,11-epoxy-steroidal aldosterone receptor antagonist described in Table 1, or eplerenone and a second amount of a compound that accelerates the outflow of aqueous humor from the anterior chamber, such as a cytoskeletal disrupting agent, prostaglandin compound, or combinations thereof, wherein the first amount and second amount together comprise a therapeutically effective amount.

In another embodiment, the present invention comprises a method for the treatment or prevention of elevated IOP comprising administering to a subject a first amount of an epoxy-steroidal aldosterone receptor antagonist, an epoxy-steroidal aldosterone receptor antagonist containing a 9,11-epoxy moiety, a 9,11-epoxy-steroidal aldosterone receptor antagonist described in Table 1, or eplerenone and a second amount of a compound that accelerates the outflow of aqueous humor from the anterior chamber, such as latanoprost, wherein the first amount and second amount together comprise a therapeutically effective amount.

In another embodiment, the present invention comprises a method for the treatment or prevention of elevated IOP comprising administering to a subject a first amount of eplerenone and a second amount of latanoprost, wherein the first amount and second amount together comprise a therapeutically effective amount.

In another embodiment, the present invention comprises a method for the treatment or prevention of elevated IOP comprising administering to a subject a first amount of an epoxy-steroidal aldosterone receptor antagonist, an epoxy-steroidal aldosterone receptor antagonist containing a 9,11-epoxy moiety, a 9,11-epoxy-steroidal aldosterone receptor antagonist described in Table 1, or eplerenone and a second amount of an anti-glaucoma agent or other compound or drug that inhibits or reduces inflow of aqueous humor, such as a cholinergic agent, sympathomimetic, carbonic anhydrase inhibitor, or combination thereof, wherein the first amount and second amount together comprise a therapeutically effective amount.

In another embodiment, the present invention comprises a method for the treatment or prevention of elevated IOP comprising administering to a subject a first amount of an epoxy-steroidal aldosterone receptor antagonist, an epoxy-steroidal aldosterone receptor antagonist containing a 9,11-epoxy moiety, a 9,11-epoxy-steroidal aldosterone receptor antagonist described in Table 1, or eplerenone and a second amount of an anti-glaucoma agent or other compound or drug selected from cannabinoids drug class, for example, anandamine; selective and unselective PKC inhibitors drug class; rho kinase inhibitors drug class; and combinations thereof; corticosteroid receptor antagonists; selective and nonselective dopamine DA-1 agonists; TNF antagonists; somatostatin selective sst4 agonists; angiotensin II antagonists; thyroxine; adenosine 3 antagonists, vacuolar proton ATPase inhibitors such as bafilomycin; sodium hydrogen antiporter inhibitors; chloride anion exchanger inhibitors; and combinations thereof, wherein the first amount and second amount together comprise a therapeutically effective amount.

In accordance with this method, an epoxy-steroidal aldosterone receptor antagonist and a second compound that accelerates the outflow of aqueous humor from the anterior chamber may be administered in various dosing regimens. For example, an epoxy-steroidal aldosterone receptor antagonist, such as an epoxy-steroidal aldosterone receptor antagonist containing a 9,11-epoxy moiety, a 9,11-epoxy-steroidal aldosterone receptor antagonist described in Table 1, or eplerenone, and a second compound that accelerates the outflow of aqueous humor from the anterior chamber, such as a cytoskeletal disrupting agent, prostaglandin compound, or combination thereof, can be administered separately, either simultaneously or sequentially. Alternatively, the epoxy-steroidal aldosterone receptor antagonist and the second compound can be administered in the form of a composition comprising both compounds. Such a composition can be, for example, a liquid composition comprising epoxy-steroidal aldosterone receptor antagonist containing a 9,11-epoxy moiety, a 9,11-epoxy-steroidal aldosterone receptor antagonist described in Table 1, or eplerenone and a second compound that accelerates the outflow of aqueous humor from the anterior chamber, such as a cytoskeletal disrupting agent, prostaglandin compound, or combinations thereof, that can be administered to a subject as topical eye drops.

In another embodiment, an epoxy-steroidal aldosterone receptor antagonist, such as an epoxy-steroidal aldosterone receptor antagonist containing a 9,11-epoxy moiety, a 9,11-epoxy-steroidal aldosterone receptor antagonist described in Table 1, or eplerenone, and a second compound that accelerates the outflow of aqueous humor from the anterior chamber, such as latanoprost, can be administered separately, either simultaneously or sequentially. Alternatively, the epoxy-steroidal aldosterone receptor antagonist and the second compound can be administered in the form of a composition comprising both compounds. Such a composition can be, for example, a liquid composition comprising epoxy-steroidal aldosterone receptor antagonist containing a 9,11-epoxy moiety, a 9,11-epoxy-steroidal aldosterone receptor antagonist described in Table 1, or eplerenone and a second compound that accelerates the outflow of aqueous humor from the anterior chamber, such as latanoprost, that can be administered to a subject as topical eye drops.

Accordingly, the present invention is further directed to compositions comprising eplerenone and latanoprost can be administered separately, either simultaneously or sequentially. Alternatively, eplerenone and latanoprost can be administered in the form of a composition comprising both compounds, such as topical eye drops.

In further accordance with this method, an epoxy-steroidal aldosterone receptor antagonist and a second compound that reduces inflow of aqueous humor into the anterior chamber may be administered in various dosing regimens. For example, an epoxy-steroidal aldosterone receptor antagonist, such as an epoxy-steroidal aldosterone receptor antagonist containing a 9,11-epoxy moiety, a 9,11-epoxy-steroidal aldosterone receptor antagonist described in Table 1, or eplerenone, and a second compound that reduces inflow of aqueous humor into the anterior chamber, such as a cholinergic agent, sympathomimetic, carbonic anhydrase inhibitor, or combination thereof, can be administered separately, either simultaneously or sequentially. Alternatively, the epoxy-steroidal aldosterone receptor antagonist and the second compound can be administered in the form of a composition comprising both compounds. Such a composition can be, for example, a liquid composition comprising epoxy-steroidal aldosterone receptor antagonist containing a 9,11-epoxy moiety, a 9,11-epoxy-steroidal aldosterone receptor antagonist described in Table 1, or eplerenone and second compound that reduces inflow of aqueous humor into the anterior chamber, such as a cholinergic agent, sympathomimetic, carbonic anhydrase inhibitor, or combination thereof, that can be administered to a subject as topical eye drops.

In another embodiment of this method, an epoxy-steroidal aldosterone receptor antagonist and a second compound that reduces IOP may be administered in various dosing regimens. For example, an epoxy-steroidal aldosterone receptor antagonist, such as an epoxy-steroidal aldosterone receptor antagonist containing a 9,11-epoxy moiety, a 9,11-epoxy-steroidal aldosterone receptor antagonist described in Table 1, or eplerenone, and a second amount of an anti-glaucoma agent or other compound or drug selected from cannabinoids drug class, for example, anandamine; selective and unselective PKC inhibitors drug class; rho kinase inhibitors drug class; and combinations thereof; corticosteroid receptor antagonists; selective and nonselective dopamine DA-1 agonists; TNF antagonists; somatostatin selective sst4 agonists; angiotensin II antagonists; thyroxine; adenosine 3 antagonists, vacuolar proton ATPase inhibitors such as bafilomycin; sodium hydrogen antiporter inhibitors; chloride anion exchanger inhibitors; and combinations thereof, can be administered separately, either simultaneously or sequentially. Alternatively, the epoxy-steroidal aldosterone receptor antagonist and the second compound can be administered in the form of a composition comprising both compounds. Such a composition can be, for example, a liquid composition comprising epoxy-steroidal aldosterone receptor antagonist containing a 9,11-epoxy moiety, a 9,11-epoxy-steroidal aldosterone receptor antagonist described in Table 1, or eplerenone and second amount of an anti-glaucoma agent or other compound or drug selected from cannabinoids drug class, for example, anandamine; selective and unselective PKC inhibitors drug class; rho kinase inhibitors drug class; and combinations thereof; corticosteroid receptor antagonists; selective and nonselective dopamine DA-1 agonists; TNF antagonists; somatostatin selective sst4 agonists; angiotensin II antagonists; thyroxine; adenosine 3 antagonists, vacuolar proton ATPase inhibitors such as bafilomycin; sodium hydrogen antiporter inhibitors; chloride anion exchanger inhibitors; and combinations thereof, that can be administered to a subject as topical eye drops.

Kits

In another embodiment, the present invention comprises a kit comprising a first compound of an epoxy-steroidal aldosterone receptor antagonist, such as an epoxy-steroidal aldosterone receptor antagonist containing a 9,11-epoxy moiety, a 9,11-epoxy-steroidal aldosterone receptor antagonist described in Table 1, or eplerenone, and a second compound that accelerates the outflow of aqueous humor from the anterior chamber, such as a cytoskeletal disrupting agent, prostaglandin compound, or combination thereof.

In another embodiment, the present invention comprises a kit comprising a first compound of an epoxy-steroidal aldosterone receptor antagonist, such as an epoxy-steroidal aldosterone receptor antagonist containing a 9,11-epoxy moiety, a 9,11-epoxy-steroidal aldosterone receptor antagonist described in Table 1, or eplerenone, and a second compound that accelerates the outflow of aqueous humor from the anterior chamber, such as latanoprost.

In another embodiment, the present invention comprises a kit comprising a first compound of eplerenone and a second compound that accelerates the outflow of aqueous humor from the anterior chamber, such as latanoprost.

In another embodiment, the present invention comprises a kit comprising a first compound of an epoxy-steroidal aldosterone receptor antagonist, such as an epoxy-steroidal aldosterone receptor antagonist containing a 9,11-epoxy moiety, a 9,11-epoxy-steroidal aldosterone receptor antagonist described in Table 1, or eplerenone, and a second compound that reduces inflow of aqueous humor into the anterior chamber, such as a cholinergic agent, sympathomimetic, carbonic anhydrase inhibitor, or combination thereof.

In another embodiment, the present invention comprises a kit comprising a first compound of an epoxy-steroidal aldosterone receptor antagonist, such as an epoxy-steroidal aldosterone receptor antagonist containing a 9,11-epoxy moiety, a 9,11-epoxy-steroidal aldosterone receptor antagonist described in Table 1, or eplerenone, and a second compound of an anti-glaucoma agent or other compound or drug selected from cannabinoids drug class, for example, anandamine; selective and unselective PKC inhibitors drug class; rho kinase inhibitors drug class; corticosteroid receptor antagonists; selective and nonselective dopamine DA-1 agonists; TNF antagonists; somatostatin selective sst4 agonists; angiotensin II antagonists; and thyroxine.

In accordance with these embodiment, the kits can be comprised of the first compound and the second compound dispensed in separate containers. For example, the kit may be comprised of eplerenone and latanoprost dispensed in separate containers. Alternatively, the kit can be comprised of a composition comprising a mixture of the first compound and the second compound in a common container. For example, the kit may be comprised of a mixture of the eplerenone and latanoprost in a common container which may be dispensed as topical eye drops.

In addition to treating glaucoma, epoxy-steroidal aldosterone receptor antagonists are also useful in treating other ocular diseases. These include ocular diseases such as low tension or normal tension glaucoma, intraocular hypertension, macular degeneration, macular edema, and diabetic retinopathy.

Other Forms of Glaucoma

Low-tension or normal tension glaucoma, where optic nerve damage occurs unexpectedly in people with normal eye pressure, can be treated with the same IOP lowering strategy as described for open angle glaucoma. Therefore epoxy-steroidal aldosterone receptor antagonists, epoxy-steroidal aldosterone receptor antagonists that contain a 9,11-epoxy moiety, 9,11-epoxy-steroidal aldosterone receptor antagonists described in Table 1, and eplerenone are useful for treatment of patients having low-tension or normal tension glaucoma.

Closed angle glaucoma, where the fluid cannot reach the outflow site, is a medical emergency treated by surgery to open an exit passage for the aqueous humor. If IOP is not normalized by the surgery, lowering aqueous inflow by administering epoxy-steroidal aldosterone receptor antagonists, epoxy-steroidal aldosterone receptor antagonists that contain a 9,11-epoxy moiety, 9,11-epoxy-steroidal aldosterone receptor antagonists described in Table 1, or eplerenone would also be rational methods for additional IOP lowering therapies.

Congenital glaucoma is usually successfully treated with surgery, but the same rationale for use of epoxy-steroidal aldosterone receptor antagonists after surgery in closed angle glaucoma would apply in congenital glaucoma. Secondary glaucomas can develop as complications of other medical conditions. Depending on the cause, epoxy-steroidal aldosterone receptor antagonists, epoxy-steroidal aldosterone receptor antagonists that contain a 9,11-epoxy moiety, 9,11-epoxy-steroidal aldosterone receptor antagonists described in Table 1, or eplerenone, are useful in treating some of these conditions. For example, corticosteriod drugs (glucocorticoids), used to treat eye inflammation and other non-ocular diseases, can trigger glaucoma in some people. Part of this effect is caused by drug-induced reduction in aqueous outflow and part may be caused by enhanced aqueous inflow via stimulation of aldosterone receptors. Epoxy-steroidal aldosterone receptor antagonist treatment in this type of secondary glaucoma would be a method to partially reverse the IOP raising effects of such drugs. In addition, administration of epoxy-steroidal aldosterone receptor antagonists allow for continued corticosteroid drug treatment in patients in need of those drugs, but who are also sensitive to the drug-induced increase in IOP.

In one embodiment, a combination of an epoxy-steroidal aldosterone receptor antagonist and an opthalmic antiinflammatory drug may be administered to a subject receiving corticosteriod drugs (glucocorticoids). This combination therapy may also be used to counteract the IOP elevating effects of the corticosteriod drugs. Drugs having utility as opthalmic antiinflammatory drugs can be used in co-therapy, co-administration, or co-formulation with a composition of epoxy-steroidal aldosterone receptor antagonists, epoxy-steroidal aldosterone receptor antagonists that contain a 9,11-epoxy moiety, 9,11-epoxy-steroidal aldosterone receptor antagonists described in Table 1, or eplerenone. Examples of opthalmic antiinflammatory drugs include lodoxamide tromethamine ophthalmic solution, sold under the trademark Alomide, (Alcon, Fort Worth, Tex.); sulfacetamide/prednisolone, sold under the trademarks Blephamide and Blephamide Liquifilm, (Allergan, Irving, Calif.); neomycin and polymyxin B sulfates and hydrocortisone ophthalmic suspension sold under the trademark Cortisporin Ophthalmic Suspension, (Monarch Pharmaceuticals, Bristol, Tenn.); Cromolyn sodium ophthalmic solution sold under the trademark Crolom, (Elan Pharmaceuticals, San Diego, Calif.); dexamethasone sodium phosphate, sold under the trademark Decadron Phosphate Ophthalmic Solution, (Merck & Co., Inc., Whitehouse Station, N.J.); prednisolone acetate sold under the trademarks Econopred, (Alcon, Fort Worth, Tex.); fluorometholone, sold under the trademarks FML Forte, FML Liquifilm, and FML-S Liquifilm, (Allergan, Irving, Calif.); loteprednol etabonate, sold under the trademark Lotemax, (Bausch & Lomb Pharmaceuticals, Tampa, Fla.); neomycin/polymyxin/dexamethasone, sold under the trademark Maxitrol, (Alcon, Fort Worth, Tex.); prednisolone acetate/sulfacetamide sodium sold under the trademark Metimyd, (Schering Corp., Kenilworth, N.J.); dexamethasone sodium phosphate/Neomycin sulfate sold under the trademark NeoDecadron Ophthalmic, (Merck & Co., Inc., Whitehouse Station, N.J.); Tobramycin/Dexamethasone sold under the trademark Tobradex, (Alcon, Fort Worth, Tex.); prednisolone sodium phosphate sold under the trademark Vasocidin, (Cooper Vision, Inc., Palo Alto, Calif.); sold under the trademark Vexol, (Alcon, Fort Worth, Tex.); rimexolone sold under the trademark Voltaren Ophthalmic, (Novartis Ophthalmics, Duluth, Ga.); and combinations thereof.

Prevention of Glaucoma

Besides people with elevated IOP, certain groups of people are at risk for developing glaucoma: people with a family history of glaucoma, persons of African descent over age 40, everyone over age 60, and diabetics. Methods or tests to define more precisely those who are at risk will likely be developed in the future. In addition to treating existing cases of glaucoma, epoxy-steroidal aldosterone receptor antagonists, epoxy-steroidal aldosterone receptor antagonists that contain a 9,11-epoxy moiety, 9,11-epoxy-steroidal aldosterone receptor antagonists described in Table 1, and eplerenone, are useful for prevention of glaucoma in well defined, at risk populations.

For example, in one embodiment, eplerenone, administered alone or in combination with one or more other compounds or drugs, can be used to prevent the onset of glaucoma in individuals susceptible to or suffering from diabetes, including, but not limited to diabetes mellitus.

Ocular Neuroprotection

Studies have strongly suggested that the Müller glial cells may play a role in the regulation of extracellular sodium and potassium ion concentrations in the eye, which could be regulated by steroid-mediated sodium uptake and its consequent effects on potassium levels. The data implicate the role of aldosterone receptors in the mechanism (Golestaneh N, et al., Epithelial sodium channel and the aldosterone receptor in cultured rat Müller glial cells, Glia. 2001 February; 33(2):160–8; Suzuki, T., et al., Molecular and Cellular Endocrinology 173 (2001) 121–125).

The regulation of sodium and potassium ion concentrations influence both edema and neuronal cell survival in the retina/macula. Edema is a significant problem in diabetic retinopathy and neurodegeneration is a big problem in glaucoma and in macular degeneration. The administration of epoxy-steroidal aldosterone receptor antagonists, epoxy-steroidal aldosterone receptor antagonists that contain a 9,11-epoxy moiety, 9,11-epoxy-steroidal aldosterone receptor antagonists described in Table 1, or eplerenone, has beneficial effects in modulating extracellular sodium and potassium ion concentrations and thereby be useful in treating macular edema, retinal cell loss, and glaucoma (optic nerve degeneration).

The ion concentrations present in the vitreous humor, in the posterior chamber of the eye, also may affect the survivability of the neuronal cells present in the eye. The administration of epoxy-steroidal aldosterone receptor antagonists, epoxy-steroidal aldosterone receptor antagonists that contain a 9,11-epoxy moiety, 9,11-epoxy-steroidal aldosterone receptor antagonists described in Table 1, or eplerenone, also has beneficial effects in modulating sodium and potassium levels in a manner which maintains an environment that promotes the survival of neuronal cells and reduces neuronal cell death.

Age-Related Macular Degeneration

Retinal nerve injury and nerve cell death occurs not only in glaucoma but also in other retinal diseases. Age-related Macular Degeneration (AMD) is a common cause of vision loss among people over the age of 60. The macula is the center of the retina, wherein exist millions of light-sensitive cells that convert light into signals that travel along nerve fibers to the brain. In AMD, for unknown reasons, the light-sensitive cells begin to die, and people start to lose central vision. Ninety percent of people with AMD have a so-called "dry" form (i.e., without edema).

AMD is the least understood major retinal disease. Although poorly understood, it is logical that the conditions or environment within the macula in which the light-sensitive cells live may affect their survival or death. A cell type known to regulate the environment surrounding the light-sensitive cells are the juxtaposed retinal glial cells. These non-neuronal cells, which are thought to carry out many "housekeeping" functions, are rich with aldosterone receptors and downstream effector system, the epithelial sodium pump (Golestaneh et al, 2001).

It is hypothesized that activation of the aldosterone receptors is involved in regulation of extracellular ion concentrations in the retina. An abnormal ionic environment is one of the known triggers for apoptosis of nerve cells, also known as programmed cell death. Hence, a novel hypothesis to explain cell death in AMD is that this ion regulating function is out of balance (i.e., over-stimulated). Blocking the aldosterone receptors with epoxy-steroidal aldosterone receptor antagonists, epoxy-steroidal aldosterone receptor antagonists that contain a 9,11-epoxy moiety, 9,11-epoxy-steroidal aldosterone receptor antagonists described in Table 1, or eplerenone, is a useful therapy for prevention of the nerve cell loss in AMD. The administration of epoxy-steroidal aldosterone receptor antagonists, epoxy-steroidal aldosterone receptor antagonists that contain a 9,11-epoxy moiety, 9,11-epoxy-steroidal aldosterone receptor antagonists described in Table 1, or eplerenone, is also a useful therapy would apply to the optic nerve damage in glaucoma as well.

The effects of epoxy-steroidal aldosterone receptor antagonists can be evaluated in models of retinal nerve cell injury and optic neuroprotection. The following articles, all incorporated by reference herein in their entirety, disclose examples of models useful for testing the effectiveness of epoxy-steroidal aldosterone receptor antagonists in regulating extracellular ion concentrations in the retina: Mizuno K, Koide T, et al., Neuroprotective effect and intraocular penetration of nipardilol, a beta-blocker with nitric oxide donative activity, Invest Ophthalmol. Vis Sci. 2001, 42(3):688–694; Morrison J C, Nylander K B et al., Glaucoma drops control intraocular pressure and protect optic nerves in a rat model of glaucoma, Invest Ophthalmol. Vis Sci 1998, 39 (3) 526–531; Matini P, Moroni F, et al., Ultrastructural and biochemical studies on the neuroprotective effects of excitatory amino acids in the ischemic rat retina, Exp Neurol 1997, 146:419–434; Osborne N N, Cazeviele C, e al., In vivo and in vitro experiments show that betaxol is a retinal neuroprotective agent, Brain Res. 1997, 751–113–123; and Unoki K, LaVail M M, Protection of the rat retina from ischemic injury by brain-revived neurotrophic factor, ciliary neuotrophic factor and basic fibroblast growth factor, Invest Ophthalmol. Vis Sci 1994, 35:907–915.

In addition to stimulating the production of aqueous humor in the anterior chamber of the eye, another affect of aldosterone is the promotion of vascular inflammation. In research on heart vasculature, Rocha et al. determined that aldosterone found that aldosterone induces a vascular inflammatory phenotype in the rat heart. Am J Physiol Heart Circ Physiol 2002 November; 283(5):H1802–10.

As vessels become inflamed, they become more permeable and fluid traveling within the vessels pass from the vessels to the surrounding tissues, increasing pressure in the extracellular regions where the vessels traverse. This results in increased edema in the affected tissues. As described below, increased edema in eye tissue, specifically retinal eye tissue can result in retinal damage.

The administration of epoxy-steroidal aldosterone receptor antagonists, epoxy-steroidal aldosterone receptor antagonists that contain a 9,11-epoxy moiety, 9,11-epoxy-steroidal aldosterone receptor antagonists described in Table 1, or eplerenone, would thereby prevent this undesirable effect by blocking aldosterone from stimlating inflammation of the vesculature in the eye, specifically the retinal tissue vesculature.

Macular Edema

Macular edema is a condition that occurs when damaged (or newly formed) blood vessels leak fluid onto the macula, a critical part of the retina for visual acuity, causing it to swell, blurring vision. Macular edema is a common problem in Diabetic Retinopathy, where retinal vessel injury causes edema, as well as in AMD (wet form), where newly formed capillaries (angiogenesis) leak fluid into the macula. Edema also occurs in the proliferative phase of diabetic retinopathy, when newly formed vessels leak fluid into either, or both, the macula and/or vitreous. An abnormal ionic environment in the extravascular space can cause leakiness of blood vessel. The aldosterone receptor regulated sodium epithelial pump in the retinal glial cells modulates the ionic concentrations in the extracellular space. Therefore, blocking the aldosterone receptor with epoxy-steroidal aldosterone receptor antagonists, epoxy-steroidal aldosterone receptor antagonists that contain a 9,11-epoxy moiety, 9,11-epoxy-steroidal aldosterone receptor antagonists described in Table 1, or eplerenone, can be used to reduce edema.

To test the hypothesis that eplerenone is useful for treating or preventing macular edema, its effects can be examined in models of edema during angiogenesis or edema caused by diabetic vascular injury. The following articles, all incorporated by reference herein in their entirety, are examples of such models: Luna J D, Chan C C, Derevjanik N L, et al., Blood-retinal barrier (BRB) breakdown in experimental autoimmune uveoretinitis: comparison with vascular endothelial growth factor, tumor necrosis factor alpha and interleukin-1 beta mediated breakdown, J Neuroscience Res 1997, 49:268–280; Aiello L P, Bursell S E, Clermont A, et al., Vascular endothelial growth factor-induced retinal permeability is mediated by protein kinase C in vivo and suppressed by an orally effective beta-isoform-selective inhibitor, Diabetes 1997, 46(9): 1473–1480; and Gilbert R E, Kelly D J, Cox A J, et al., Angiotensin converting enzyme inhibition reduces retinal overexpression of vascular endothelial growth factor and hyperpermeability in experimental diabetes, Diabeologia 2000, 43(11):1360–1367.

Administration of Epoxy-Steroidal Aldosterone Receptor Antagonists

Epoxy-steroidal aldosterone receptor antagonists, epoxy-steroidal aldosterone receptor antagonists that contain a 9,11-epoxy moiety, 9,11-epoxy-steroidal aldosterone receptor antagonists described in Table 1, or eplerenone can be topically administered using either eye drops or systemic (e.g., oral, intravenous, transdermal, percutaneous, etc.) administration in therapeutically effective dosages. The epoxy-steroidal antagonists can also be administered in a therapeutically effective amount directly into the eye by injection or by the use of appropriate devices for administration (e.g., a syringe or other forced flow device).

Preferred methods of administration for glaucoma would be topically onto the eye, via eyedrops, or orally. For retinal diseases, the epoxy-steroidal aldosterone receptor antagonists, epoxy-steroidal aldosterone receptor antagonists that contain a 9,11-epoxy moiety, 9,11-epoxy-steroidal aldosterone receptor antagonists described in Table 1, or eplerenone can also be administered topically or orally.

As an example, oral doses of eplerenone may be provided at 0.1–2000 mg/day. In another embodiment, oral doses of eplerenone may be administered at 0.5–500 mg/day. In another embodiment, oral doses of eplerenone may be administered at 0.75–400 mg/day. In another embodiment, oral doses of eplerenone may be administered at 1–250 mg/day. In still another embodiment, oral doses of eplerenone may be administered at 25–200 mg/day.

The total daily dose of each drug can be administered to the patient in a single dose, or in proportionate multiple subdoses.

When an aldosterone receptor antagonist such as an epoxy-steroidal aldosterone receptor antagonist, an epoxy-steroidal aldosterone receptor antagonist that contains a 9,11-epoxy moiety, an epoxy-steroidal aldosterone receptor antagonist that contains a 9,11-epoxy moiety and described in Table 1, or eplerenone is administered in combination with another compound or drug having IOP reducing properties, the dosage of either the aldosterone receptor antagonist, such as eplerenone, the coadminstered compound or drug, or both may be lowered. For example, while a 0.005% solution of Xalatan (latanoprost), when administered alone, is topically given as in a dose of one drop per day (abut 30 microliters), the preferred daily dosage of either eplerenone, Xalatan, or both, will typically be lower than the dosage recommended for conventional monotherapeutic treatment.

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

What is claimed is:

1. A method of reducing intraocular pressure in a subject having elevated intraocular pressure or having a condition which places them at risk for elevated intraocular pressure, comprising administering a therapeutically effective amount of eplerenone to the subject.

2. The method of claim 1 further comprises administering a therapeutical effective amount of second ingredient, wherein the second ingredient is a compound that accelerates the outflow of aqueous humor from the anterior chamber selected from the group consisting of prostaglandin compounds.

3. The method of claim 2 wherein the prostaglandin compound is selected from the group consisting of PGA, PGB, PGD, PGE, PGF, their derivatives, latanoprost, a combination of latanoprost and timilol, unoprostone isopropyl ophthalmic solution, lumigan, travaprost, unoprostone, $PGF2_\alpha$ agonists, prostanoids, prostaglandin pro-drugs, and combinations thereof.

4. A method of reducing intraocular pressure in a subject having elevated intraocular pressure or having a condition which places them at risk for elevated intraocular pressure, comprising administering a therapeutically effective amount of eplerenone and latanoprost.

5. A method of reducing intraocular pressure in a subject having elevated intraocular pressure by modulating intraocular levels of ions in a subject, comprising administering eplerenone to the subject.

6. The method of claim 5 wherein the ions are selected from the group consisting of sodium and potassium.

7. A method of reducing intraocular pressure in a subject having elevated intraocular pressure comprising coadministering eplerenone and a second compound that accelerates the outflow of aqueous humor from the anterior chamber, wherein the second compound is selected from the group consisting of prostaglandin compounds.

8. The method of claim 7 wherein the prostaglandin compound is selected from the group consisting of PGA, PGB, PGD, PGE, PGF, their derivatives, latanoprost, a combination of latanoprost and timilol, unoprostone isopropyl ophthalmic solution, lumigan, travaprost, unoprostone, $PGF2_\alpha$ agonists, prostanoids, prostaglandin pro-drugs, and combinations thereof.

9. The method of claim 8 wherein the prostaglandin compound is latanoprost.

10. The method of claim 9, wherein the eplerenone and lantoprost are administered separately, either simultaneously or sequentially.

11. The method of claim 9, wherein the eplerenone and latanoprost are administered in the form of a composition comprising both eplerenone and latanoprost.

12. The method of claim 11, wherein the composition is a liquid composition comprising eplerenone and latanoprost that is administered to a subject as topical eye drops.

* * * * *